(12) United States Patent
Zambelli (10) Patent No.: US 10,820,892 B2
(45) Date of Patent: Nov. 3, 2020

(54) BONE BIOPSY DEVICE

(71) Applicant: Roberto Zambelli, Rho (IT)

(72) Inventor: Roberto Zambelli, Rho (IT)

( * ) Notice: Subject to any disclaimer, the term of this patent is extended or adjusted under 35 U.S.C. 154(b) by 465 days.

(21) Appl. No.: 15/820,479

(22) Filed: Nov. 22, 2017

(65) Prior Publication Data

US 2018/0140285 A1    May 24, 2018

(30) Foreign Application Priority Data

Nov. 24, 2016   (IT) .................. 102016000119028

(51) Int. Cl.
*A61B 10/02*       (2006.01)
*A61B 90/00*       (2016.01)

(52) U.S. Cl.
CPC ........ *A61B 10/025* (2013.01); *A61B 10/0266* (2013.01); *A61B 2010/0258* (2013.01); *A61B 2090/036* (2016.02); *A61B 2562/12* (2013.01)

(58) Field of Classification Search
None
See application file for complete search history.

(56) References Cited

U.S. PATENT DOCUMENTS

| | | | |
|---|---|---|---|
| 4,785,826 A | 11/1988 | Ward | |
| 5,954,671 A * | 9/1999 | O'Neill | A61B 17/1637 600/567 |
| 2004/0077973 A1 * | 4/2004 | Groenke | A61B 10/025 600/567 |
| 2010/0204611 A1 * | 8/2010 | Zambelli | A61B 10/025 600/567 |
| 2014/0081318 A1 * | 3/2014 | Houser | A61B 17/0057 606/213 |

FOREIGN PATENT DOCUMENTS

| | | |
|---|---|---|
| EP | 1 175 866 A2 | 1/2002 |
| EP | 2 215 971 A1 | 8/2010 |
| WO | 93/19675 A1 | 10/1993 |
| WO | 2012/015770 A2 | 2/2012 |

OTHER PUBLICATIONS

IT Search Report, dated Aug. 25, 2017, from corresponding IT 201600119028 application.

* cited by examiner

*Primary Examiner* — Jacqueline Cheng
*Assistant Examiner* — Jairo H Portillo
(74) *Attorney, Agent, or Firm* — Nixon & Vanderhye (57) ABSTRACT

A bone biopsy device includes an outer cannula having a mouth with a cutting edge to section a frustule of spongy bone, a plate mounted slidably within the cannula with a semi-cylindrical portion at its end, and a stylet mounted slidably within the plate and having a pointed tip protruding from the mouth of the cannula to pierce the bone. The mouth has a narrowing and the semi-cylindrical part of the plate has at its end at least one pair of opposed lunettes/anchorages bendable, with respect to a horizontal plane, towards the interior of the semi-cylindrical portion when they encounter the narrowing of the mouth, thereby occluding the lumen of the plate and clasp the base of the sectioned frustule and allow extraction of the frustule by way of the plate whilst the cannula is kept at the operating site, allowing aspiration of marrow after the frustule has been removed.

15 Claims, 12 Drawing Sheets

BONE BIOPSY DEVICE

BACKGROUND OF THE INVENTION

Field of the Invention

The present invention refers to the field of bone biopsy.

In simplified terms, the bone consists of a hard (compact or cortical) outer part and a porous (spongy or trabecular bone) inner part containing the marrow in its pores. Bone biopsy consists in sampling the inner part of the bone to ascertain the nature and development of blood cells (haemopoiesis). By removing an inner fragment of trabecular bone, in the form of a cylindrical plug (frustule), the cells in their various stages of maturation, useful for diagnosing haemato-oncological diseases, are removed therewith.

Description of the Related Art

Various types of bone biopsy devices adapted to remove a frustule of spongy tissue for subsequent laboratory diagnostic tests are commercially known.

A bone biopsy device generally comprises a cylindrical cannula with a sharpened, cutting mouth within which is disposed a mandrel or stylet provided with a perforating tip which protrudes from the cannula mouth to pierce the compact bone. Once the tip of the stylet has pierced the compact bone, the stylet is extracted from the cannula and the cannula is advanced into the spongy bone, so as to section a frustule of spongy bone in the mouth of the cannula. At this point the physician carries out a rocking movement of the cannula to break the base of the frustule (luxation) that is to be removed. The cannula is then extracted from the bone, carrying the sectioned frustule inside it. Finally, an extraction rod (probe) is inserted into the mouth of the cannula to push the removed frustule towards the rear of the cannula and cause it to exit the instrument.

Such a bone biopsy system presents various drawbacks. The main drawback is due to the numerous frustules which are lost when they slip out of the mouth of the cannula as it is extracted from the patient.

Another drawback is represented by the fact that besides collecting the frustule, the physician generally has to sample marrow (blood) from inside the bone. In current biopsy instruments, this blood sampling must obligatorily be done before sectioning the frustule, otherwise the previously sectioned frustule would obstruct the mouth of the cannula, preventing aspiration of the marrow. As a result, the frustule that will subsequently be made will be deprived of blood cells which are important for the diagnostic examination. Consequently, the physician frequently has to perform two separate samplings with two different instruments: one for marrow sampling and the other for frustule sampling.

The "needles" for bone biopsy currently available commercially are therefore limited to coring of the frustule which will be recovered from the interior of the cannula only after having extracted it from the patient and the marrow aspirate will follow later with a separate intervention and appropriate needle.

In order to overcome the disadvantages of these devices the Applicant has developed a device for bone biopsy, currently known as needle for bone biopsy, the object of the patent EP2215971B1.

The device described in EP2215971B1 is apt to core and remove a "frustule" of trabecular bone inside the bones of patients suffering from haemato-oncological-problems, and allows at the same time aspiration by means of a syringe of the bone marrow (therefore in a single biopsy+marrow aspiration intervention) after having removed the frustule, thanks to the possibility of leaving the milling cannula temporarily in place.

This device comprises in fact an external cannula with a milling mouth, a plate mounted slidably inside the cannula and provided with a semi-cylindrical portion at its distal end, and a pointed stylet mounted slidably inside the plate, where the semi-cylindrical part of the plate has at its distal end a pair of opposite circumferential sets of teeth, in the form of wings apt to bend radially towards the interior when they encounter the internal narrowing of the mouth of the cannula.

Therefore in order to be able to sample the frustule penetrated inside the milling cannula by means of the manoeuvre of coring of the device described in EP2215971B1, the semi-cylindrical part of the plate is made to move forwards in the narrowing of the mouth until the teeth narrow, choking the frustule at the base, then withdrawing the plate from the cannula to remove the frustule contained in said semi-cylindrical part.

However this device, although overcoming the disadvantages of the previous devices, has some drawbacks. The Applicant has in fact observed that when the abovementioned device is used on elderly persons a considerable percentage of removal failures occur due to the fact that trabecular bone has become fragile and "soft" and therefore not suitable for being trapped by the teeth described above.

SUMMARY OF THE INVENTION

Object of the present invention is to overcome the drawbacks of the prior art by providing an improved bone biopsy device that is safe, reliable and is not traumatic or invasive for the patient.

Another object of the present invention is to provide such a device that is able to perform sampling of a frustule of bony tissue, without damage thereto, also in the case of fragile and "soft" bone tissue like that of elderly persons, reducing or better still cancelling the percentage of failures of removal of the trabecular bone.

Another object of the present invention is to provide such a device that allows removal of the frustule whilst leaving the cannula in place, thus allowing aspiration of the bone marrow after and not before sectioning the frustule.

Another object of the present invention is to provide such a device that is compact and simple and rapid to use for the physician.

These objects are achieved in accordance with the invention with the characteristics listed in appended independent claim 1.

Advantageous embodiments of the invention are apparent from the dependent claims.

The term proximal will henceforth be used to identify the parts of the device destined to face towards the operator, whereas the term distal denotes the parts of the device destined to face towards the patient during the procedure.

The bone biopsy device according to the invention comprises:

an external cannula provided with a mouth with a cutting edge to section a frustule of the spongy part of the bone,
a plate mounted slidably in the cannula and provided with
a semi-cylindrical portion at its distal end, and a stylet (or mandrel) mounted slidably inside the plate and provided with a pointed tip which protrudes from the mouth of the cannula to pierce the compact part of the bone.

The mouth of the cannula has on its inside a narrowing and the semi-cylindrical part of the plate has at its distal end at least a pair of small anchorages opposite with respect to a horizontal plane and adapted to bend with respect to said horizontal plane, when they encounter the narrowing of the mouth, so as to clasp the base of the sectioned frustule and allow extraction of the frustule by means of the plate whilst maintaining the cannula in the operating site.

BRIEF DESCRIPTION OF THE DRAWINGS

Further characteristics of the invention will be made clearer by the detailed description that follows, referring to a purely exemplifying and therefore non limiting embodiment thereof, illustrated in the appended figures, wherein.

DESCRIPTION OF THE PREFERRED EMBODIMENTS

The device for bone biopsy and bone marrow aspiration according to the invention, designated as a whole with reference numeral 1, is described with the aid of the figures.

Figure 1:
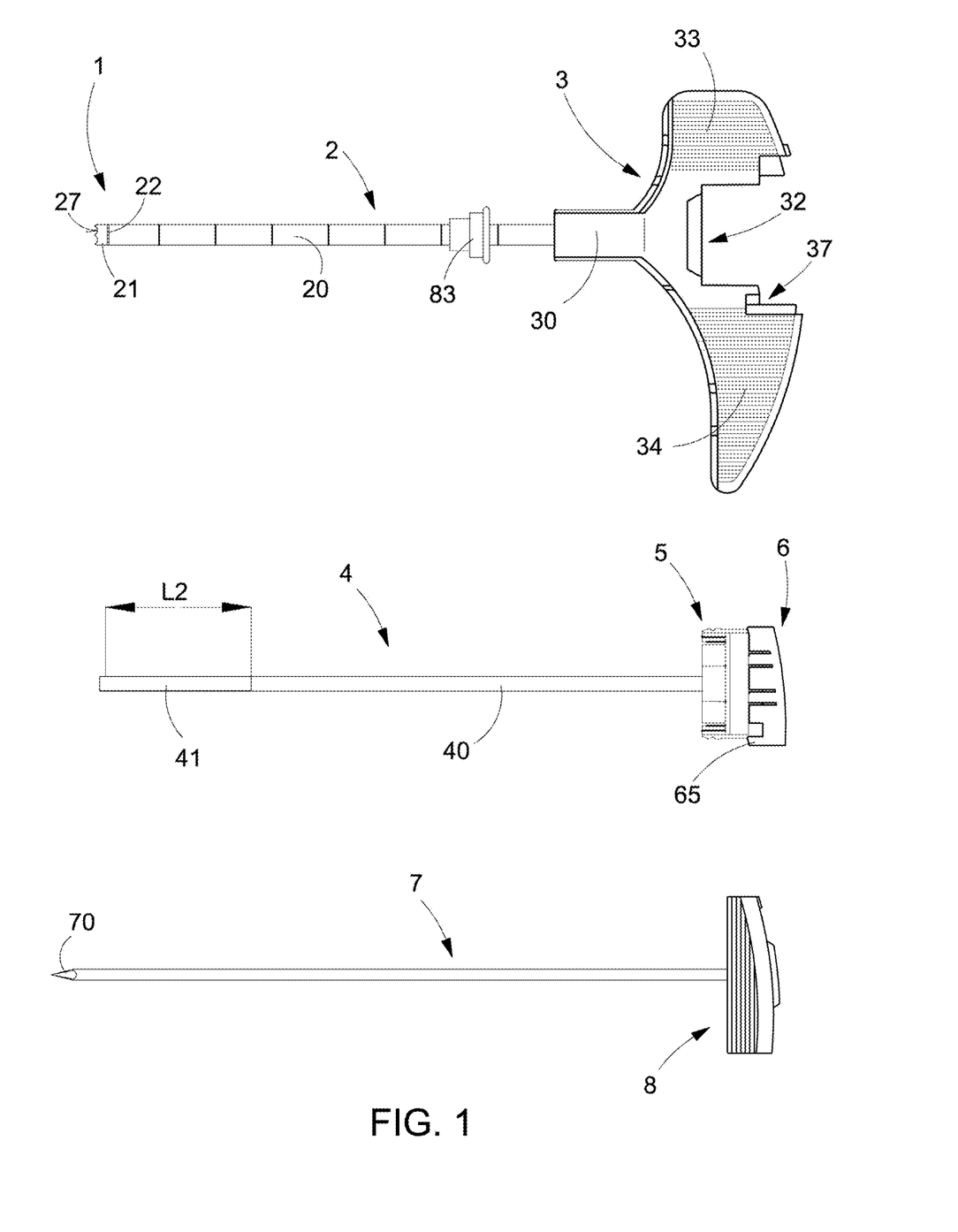
FIG. 1 is a side view illustrating the three components (cannule, plate and stylet) of the biopsy device according to the invention exploded.

With reference for now to FIG. 1, the device 1 comprises an outer cannula 2, a plate 4 adapted to be inserted axially inside the cannula 2, and a stylet or mandrel 7 adapted to be inserted axially into the plate 4.

The proximal end of the cannula 2 is fixed to a handgrip 3. The proximal end of the plate 4 is fixed to a support 5 on which is mounted a latch 6. The proximal end of the stylet 7 is fixed to a closing support 8.

The cannula 2 consists of a cylindrical metal tube 20 and can be advantageously also a cannula divided into centimetres (FIG. 1), similarly to other biopsy instruments known in the art, with stopper.

In the case of cannula 2 divided into centimetres, the outer surface of the cannula is provided with notches or with simple small lines, placed at a predetermined distance one from the other, and also provided with a sliding element or stopper 83 fitted on said cannula 2, which can be positioned at the doctor's discretion at a certain distance from the skin of the patient, apt to stop the penetration in the bone of the cannula 2 at the required depth during the coring of the frustule so as to allow the control of the advance.

Figure 2:
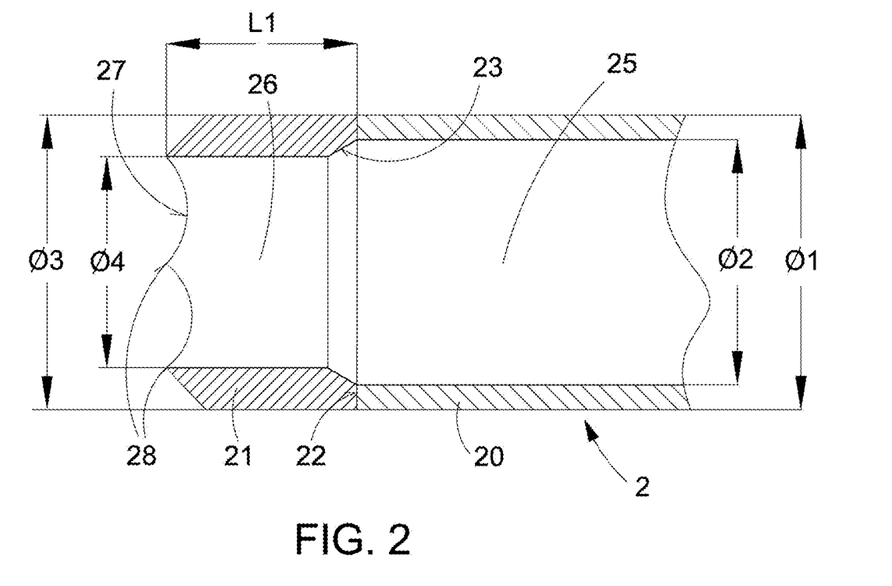
FIG. 2 is an enlarged axial sectional view, illustrating the mouth of the cannula of the device of FIG. 1.

Said cylindrical metal tube 20 of said cannule 2 is hollow on the inside so as to define an axial channel 25 (FIG. 2).

As shown in FIG. 2, the cannula tube 20 has an outer diameter $\phi 1$ and an inner diameter $\phi 2$.

A mouth 21 is fixed, by laser welding 22, on the edge of the distal end of the cannula tube 20. The mouth 21 has a hollow cylindrical shape so as to define an axial chamber 26. The mouth 21 has an outer diameter $\phi 3$, an inner diameter $\phi 4$ and a length L1.

The outer diameter $\phi 3$ of the mouth 21 is equal to the outer diameter $\phi 1$ of the cannula tube 20.

The inner diameter $\phi 4$ of the mouth 21, on the other hand, is slightly smaller than the inner diameter $\phi 2$ of the cannula tube 20. In this manner, a narrowing is defined in the passage from the channel 25 of the tube 20 to the chamber 26 of the mouth 21. The proximal end of the mouth 21 has a suitably flared portion 23. In this manner, the narrowing between the channel 25 of the tube 20 and the mouth 21 of the cannula is defined by a short tapered transition area 23.

The mouth 21 has a distal end edge 27 suitably tapered so as to be sharp and cutting in order to be able to penetrate the bone. The cutting edge 27 of the mouth has a profile with a plurality of adjacent arcs of a circle, so as to define a plurality of tips 28 able to scratch and cut the bone. The total length L1 of the mouth 21 is about 2-3 mm.

Figure 3:
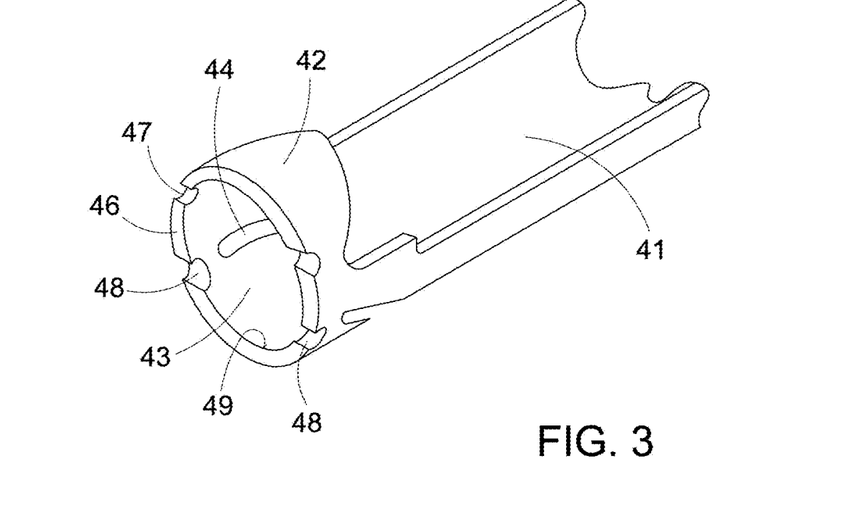
FIG. 3 is a perspective view illustrating a distal end portion of the plate of the device of FIG. 1, provided with specific grip elements.
Figure 4:
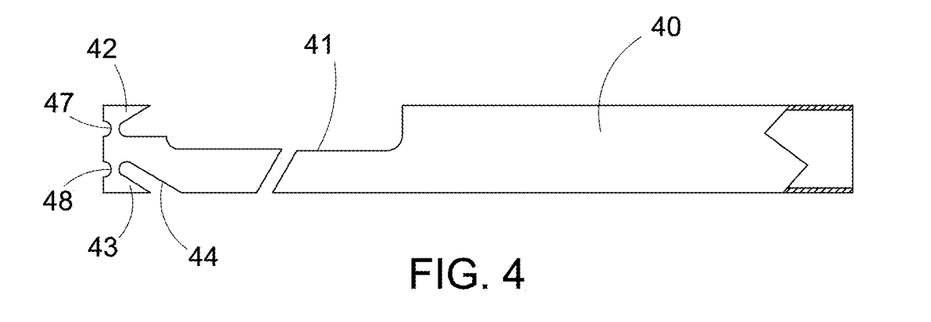
FIG. 4 is a side view, partially interrupted, of the plate of FIG. 3.
Figure 5A:
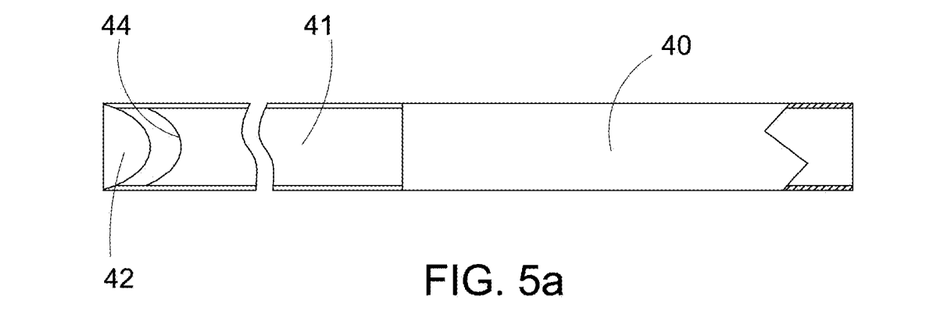
FIGS. 5a and 5b are, respectively, a view from above and from below of the plate of FIG. 3, partially interrupted.
Figure 5B:
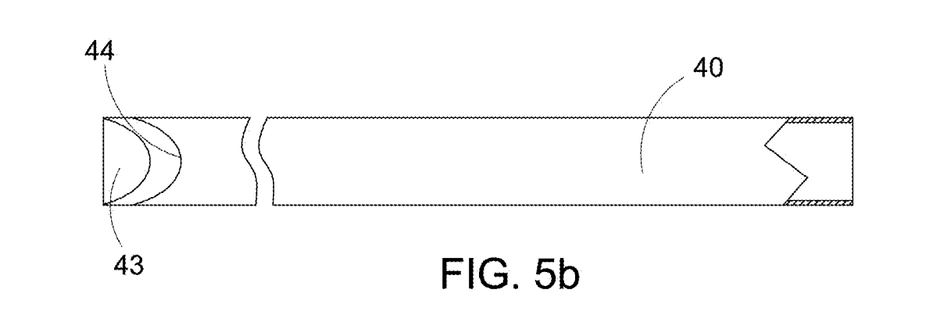

With reference to FIGS. 1, 3 and 4, the plate 4 consists of a metal tube 40 with an outer diameter slightly smaller than the inner diameter $\phi 2$ tube 20 of the cannula, so as to be able to slide guided coaxially inside the tube 20 of the cannula. A distal portion of the tube 40 of the plate is cut axially for a length L2, so as to obtain a substantially semi-cylindrical portion or section 41. The semi-cylindrical portion 41 has a length L2 of about 3-4 cm.

At the distal end of said semi-cylindrical portion 41, and integral with said cylindrical portion 41, a circular continuous ring or edge 46 is placed (FIG. 3) with a lumen 49 corresponding to the lumen of said tube 40 of said plate 4, as illustrated in FIGS. 3, 4.

From said circular continuous edge 46, and integral therewith, flexible grip elements branch off comprising an upper anchorage or lunette 42 and a lower anchorage or lunette 43, each one provided with a sharp inner cutting edge, which are placed in an opposed manner with respect to a horizontal plane, more particularly the horizontal plane whereon the longitudinal axis of said plate 4 lies and/or the transverse horizontal axis of said circular continuous edge 46.

On an area of the semi-cylindrical portion 41 of the plate 4, at the lower lunette 43, a slot 44 is then provided.

A pair of upper recesses 47 and a pair of lower recesses 48 are formed on said distal circular edge 46 of the plate 4, at the zones of attachment of the two lunettes 42, 43, in order to make said lunettes 42, 43 more flexible.

During use, when the plate 4 is made to move forwards in the channel 25 of the cannula towards the chamber 26, as will be later explained in detail, the two lunettes 42, 43 are pushed into the narrowing 21 of said chamber 26 (FIG. 6*b*), bending towards the interior of the semi-cylindrical body 41, with respect to said horizontal plane, when they encounter the tapered transition zone 23.

Figure 6A:
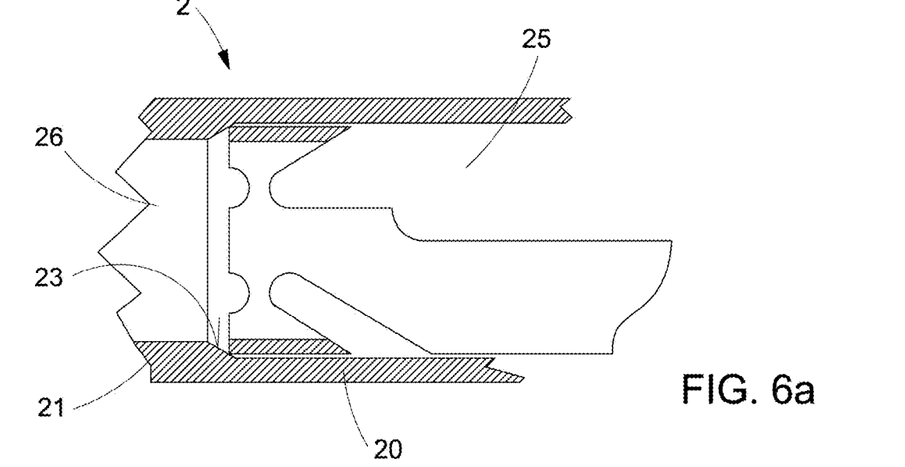
FIGS. 6a and 6b are vertically sectioned views of the distal end portion of the mouth, respectively before and after the transit of the plate in the narrowing of the mouth of the cannula of FIG. 2.
Figure 6B:
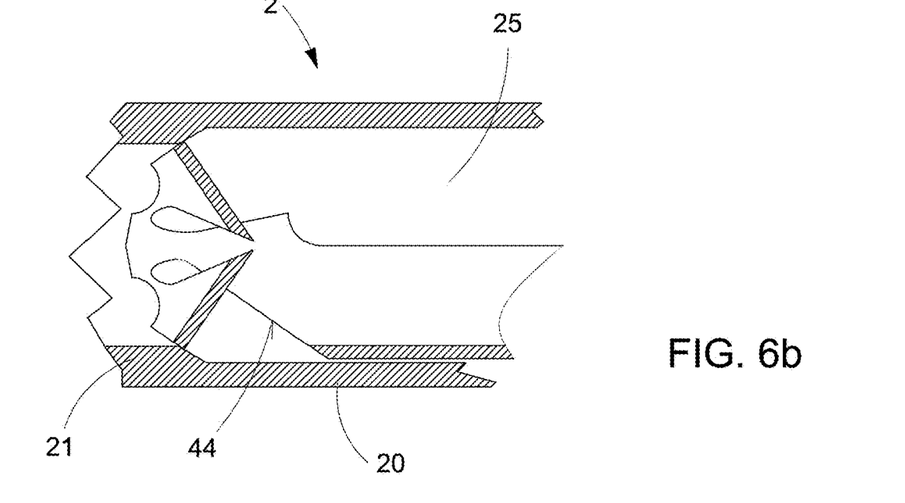

In this way the simultaneous introflection takes place of said upper lunette 42 towards the interior of the semi-cylindrical body 41 and of said lower lunette 43 inside the slot or lower opening 44 formed on said lower semi-cylindrical portion 41, in a similar manner to the grips joined as hinge of pliers.

Figure 7:
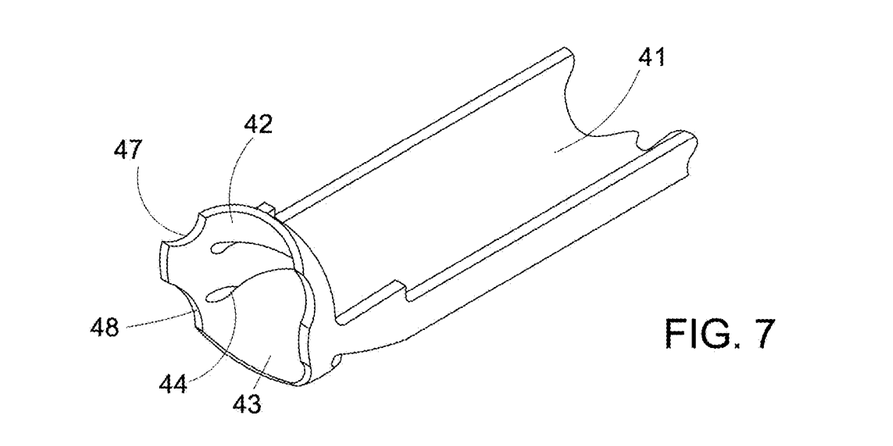
FIG. 7 is a perspective view of the distal end portion of the plate of FIG. 6b.

The simultaneous introflection of the two opposing lunettes 42, 43 cause the occlusion of the lumen 49 of the lower semi-cylindrical portion 41 (FIG. 7) allowing the removal of the frustule without, or virtually without, failures.

The Applicant has in fact found that, in place of the radial wings with pointed teeth which bend radially described in EP2215971B1, the part which traps the base of the frustule is configured with flexible horizontal lunettes as described above, there is a considerable reduction in the failures of removal of fragile and "soft" trabecular bones such as those present in elderly people.

Figure 9:
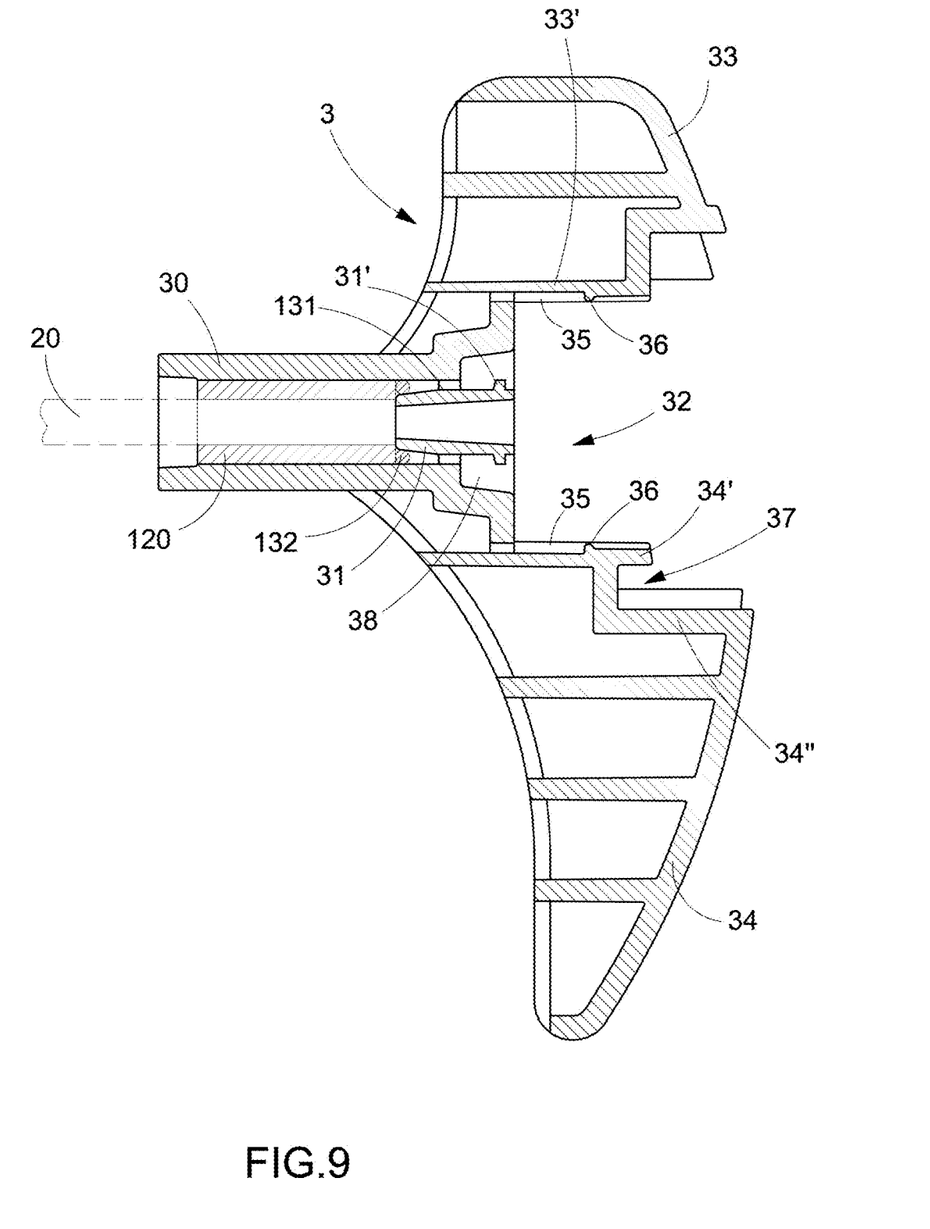
FIG. 9 is an axial sectional view of the grip of the device of FIG. 1.

With reference to FIGS. 1 and 9, the handgrip 3 has a cylindrical tang 30 in which is fixed, by gluing, co-moulding in plastic or another method, a metal cylinder 120 inside which is welded the proximal end part of the tube 20 of the cannula. A conical connector 31 of the Luer Lock type is provided in the proximal end of the tang 30 of the handgrip. The conical connector 31 has two radial wings 31' disposed in diametrically opposite positions, serving as a thread to allow the tip of a medical instrument, such as a syringe for bone marrow aspiration, to be screwed on.

It should be noted that the Luer Lock cone 31 is obtained by moulding directly in the handgrip 3. For this purpose, beneath the wings 31' of the Luer Lock cone there are left two side holes 131 which are closed by a ring 132 which is pressed into the seat provided for this purpose, during assembly of the instrument. This solution allows a considerable lowering of costs, compared with the prior art in which the Luer Lock cone is obtained as an extension of the metal cylinder welded to the proximal end of the biopsy cannula.

Two portions 33 and 34 of the handgrip depart in diametrically opposite directions from the tang 30. The second portion 34 of the handgrip is longer than the first portion 33 and has a curved profile so as to obtain an ergonomic handgrip.

At the proximal end of the tang 30, between the two portions 33 and 34 of the handgrip, a seat 32 is defined able to accommodate the plate support 5 and the latch 6. The seat 32 is defined between two opposite walls 33' and 34' of the handgrip portions 33 and 34. Respective guide grooves 35 which have a locking protrusion 36 are formed in the walls 33' and 34'.

In the second portion of handgrip 34, behind the wall 34', is formed a seat 37, U-shaped in cross section, disposed between the part 34' and a second part 34" of the portion of handgrip 34.

Figure 10:
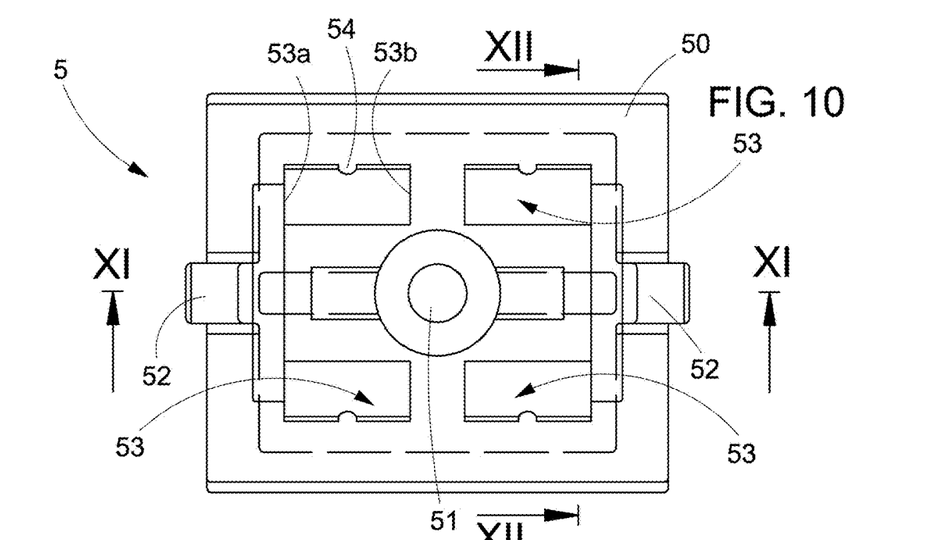
FIG. 10 is a view from the rear of the support of the plate of the device of FIG. 1.
Figure 11:
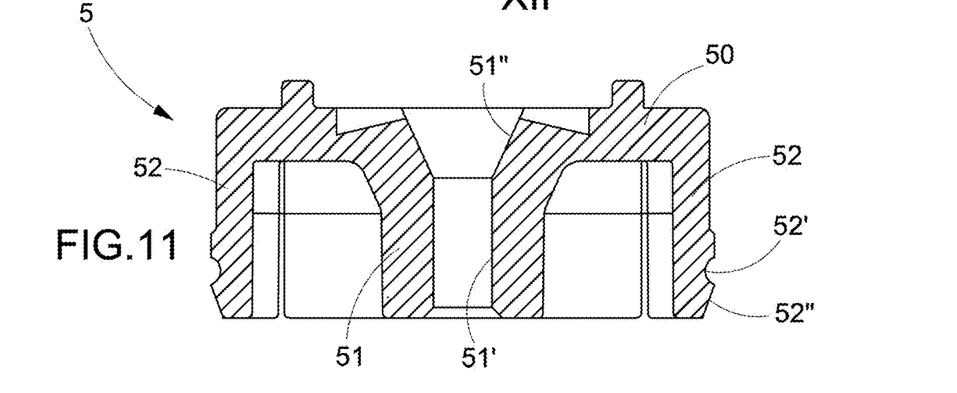
FIGS. 11 and 12 are two sectional views taken respectively along the planes of section XI-XI and XII-XII of FIG. 10.
Figure 12:
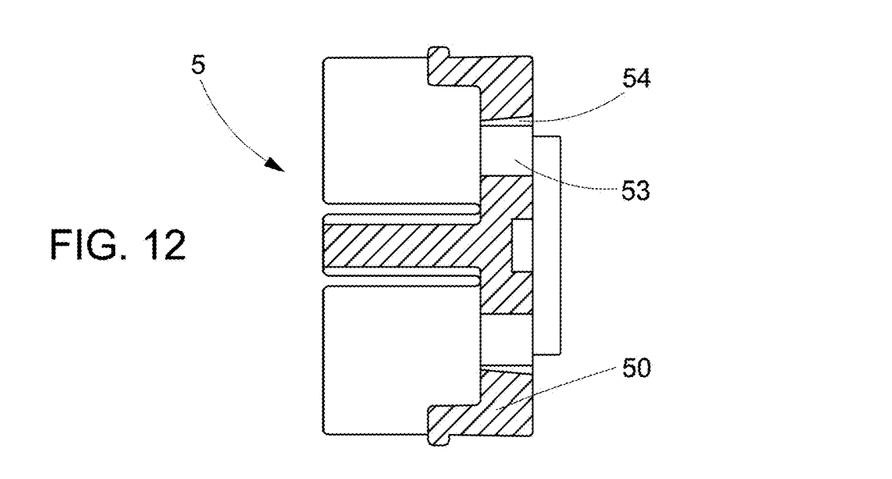

With reference to FIGS. 10, 11, 12, the support 5 of the tube 40 of the plate comprises a body 50 substantially shaped as a rectangular plate. A tang 51 is formed in the centre of the body 50, defining a hole 51' provided with a tapered portion 51". The proximal end of the tube 40 of the plate is blocked in the hole 51, for example by depositing a suitable drop of glue in the flared part 51" of the tang 51.

Two flexible wings 52 disposed in diametrically opposite directions with respect to the tang 51 are situated at the edges of the two minor sides of the body 50. A groove 52' is formed in the outer surface of the wings 52. The surface 52" of the end part of each wing 52 is suitably tapered. In this manner, when the support 5 is inserted in the seat 32 of the handgrip 3, the flexible wings 52 of the support slide in the guide grooves 35 of the handgrip, bending inwards, until the grooves 52' of the wings of the support 5 are snap engaged by the stopping ribs 36 of the handgrip.

Four slots 53 are formed in the body 50 of the support 5. Each slot 53 defines a rear abutment edge 53*a* and a front abutment edge 53*b*. A protrusion 54, disposed in an intermediate position, is formed on a longitudinal edge of each slot 53.

Figure 13:
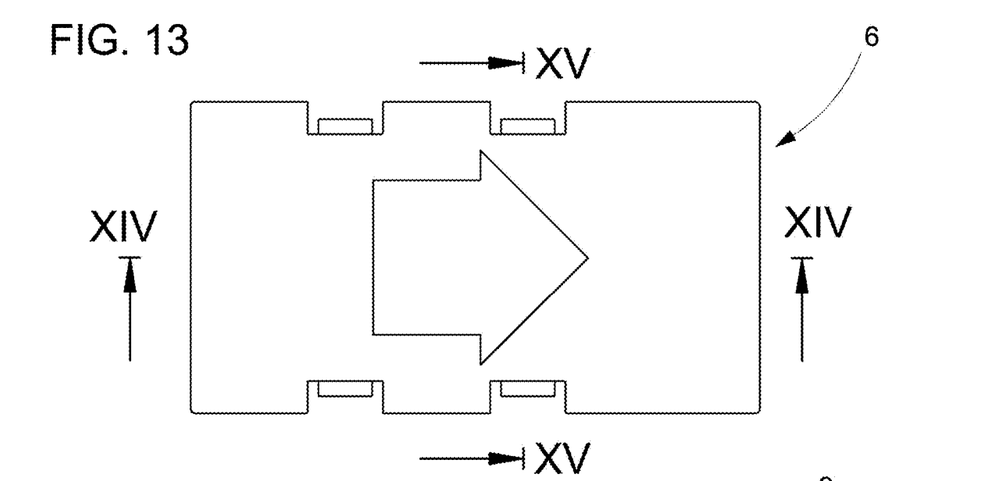
FIG. 13 is a view from the rear of the latch mounted on the support of the plate of the device of FIG. 1.
Figure 14:
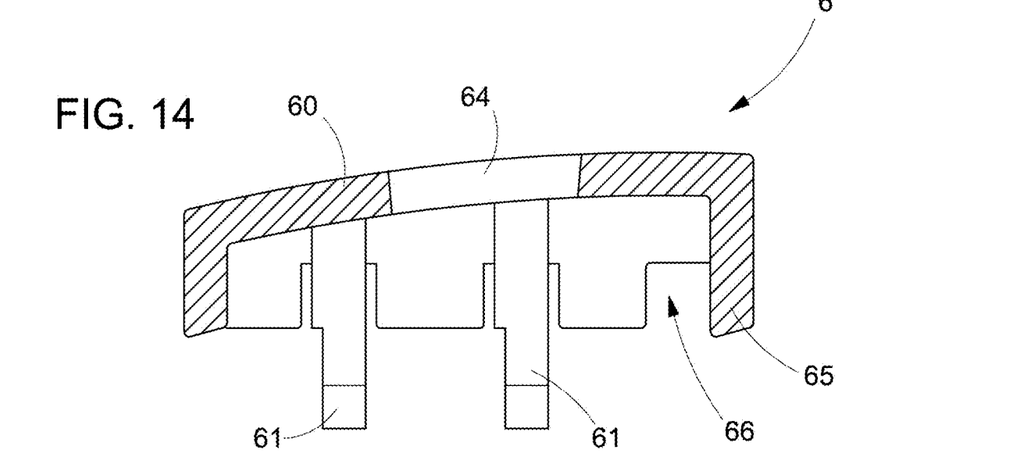
FIGS. 14 and 15 are two sectional views taken respectively along the planes of section XIV-XIV and XV-XV of FIG. 13.
Figure 15:
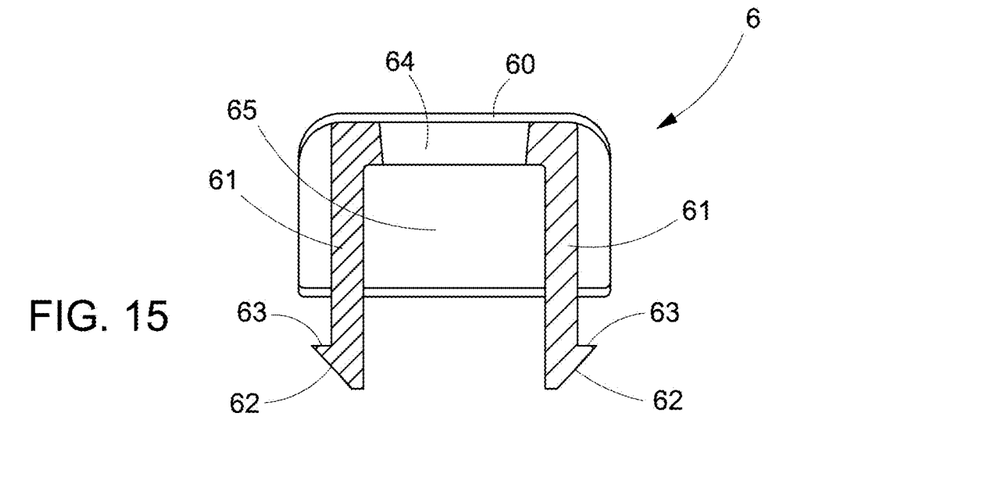

With reference to FIGS. 13, 14 and 15, the latch 6 comprises a substantially rectangular, slightly curved body 60. The body 60 of the latch is slightly longer and slightly narrower than the body 50 of the support 5. Four flexible wings 61 are formed in the edges of the two major sides of the body 60 of the latch, two on each side. Each flexible wing 61 has a tapered end 62 which defines a retaining surface 63. In this manner, the wings 61 of the latch can engage in the respective slots 53 of the support 5 and the latch 6 is retained on the support 5 by means of the retaining surfaces 63 of the wings 61 which abut against the edges of the slots 53 of the support.

An arrow 64 which indicates the direction of operation of the latch 6 to be able to arm the biopsy device 1 is formed on the body 60 of the latch. A blocking rib 65 which defines a U-shaped groove 66 is provided in the side edge of the body 60 pointed at by the arrow 64.

When the latch 6 is in the closing position, its wings 61 abut against the rear abutment surface 53*a* of the slots 53 of the support and do not overcome the intermediate protrusion 54 in the respective slot 53 of the support. In this situation the U-shaped groove 66 of the latch is covered by the body of the support 5 and the rib 65 of the latch is level with the wall 34' (FIG. 3) of the seat 32 of the handgrip. Consequently, the latch 6 integral with the support 5 of the plate cannot be pushed into the seat 32 of the handgrip.

On translating the latch in the direction of the arrow 64, the wings 61 of the latch slide in the slots 53 of the support, going beyond the intermediate protrusion 54 of the slots and abutting against the front wall 53*b* of the slot 53. As a result, the U-shaped groove 66 of the latch protrudes with respect to the body of the support 5, placing itself in register with the wall 34' of the handgrip and the rib 65 of the latch is situated level with the seat 37 of the handgrip. In this manner, the assembly formed by the support 5 and the latch 6 can be pushed into the seat 32 of the handgrip 3.

Figure 16:
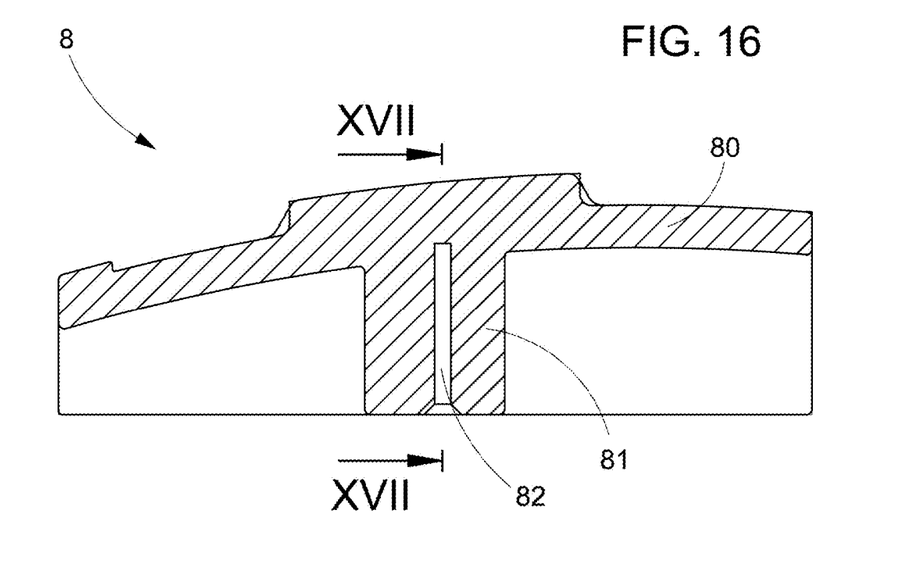
FIG. 16 is a view in longitudinal section of the support of the stylet of the device of FIG. 1.
Figure 17:
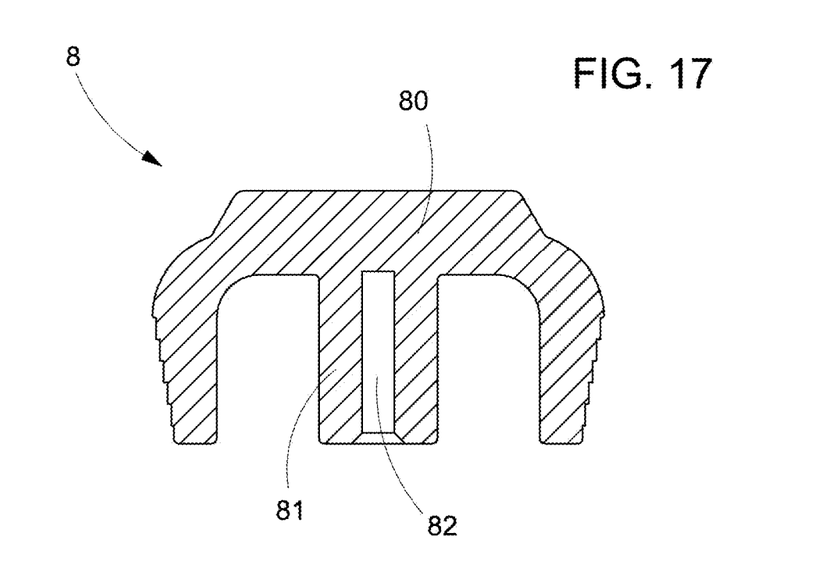
FIG. 17 is a cross sectional view, taken along the plane of section XVII-XVII of FIG. 16.

With reference to FIGS. 16-17, the closing support 8 comprises a substantially rectangular body 80, slightly curved so as to continue the radius of curvature that joins the two portions 33 and 34 of the handgrip. In this manner the closing support 8 acts as a cover and perfectly covers the latch 6. A tang 81 provided with a hole 82 in which is fixed the proximal end of the stylet 7 is formed in the central part of the body 80.

Operation of the bone biopsy device 1 is described with reference in particular to FIGS. 8, 18-20.

Figure 8:
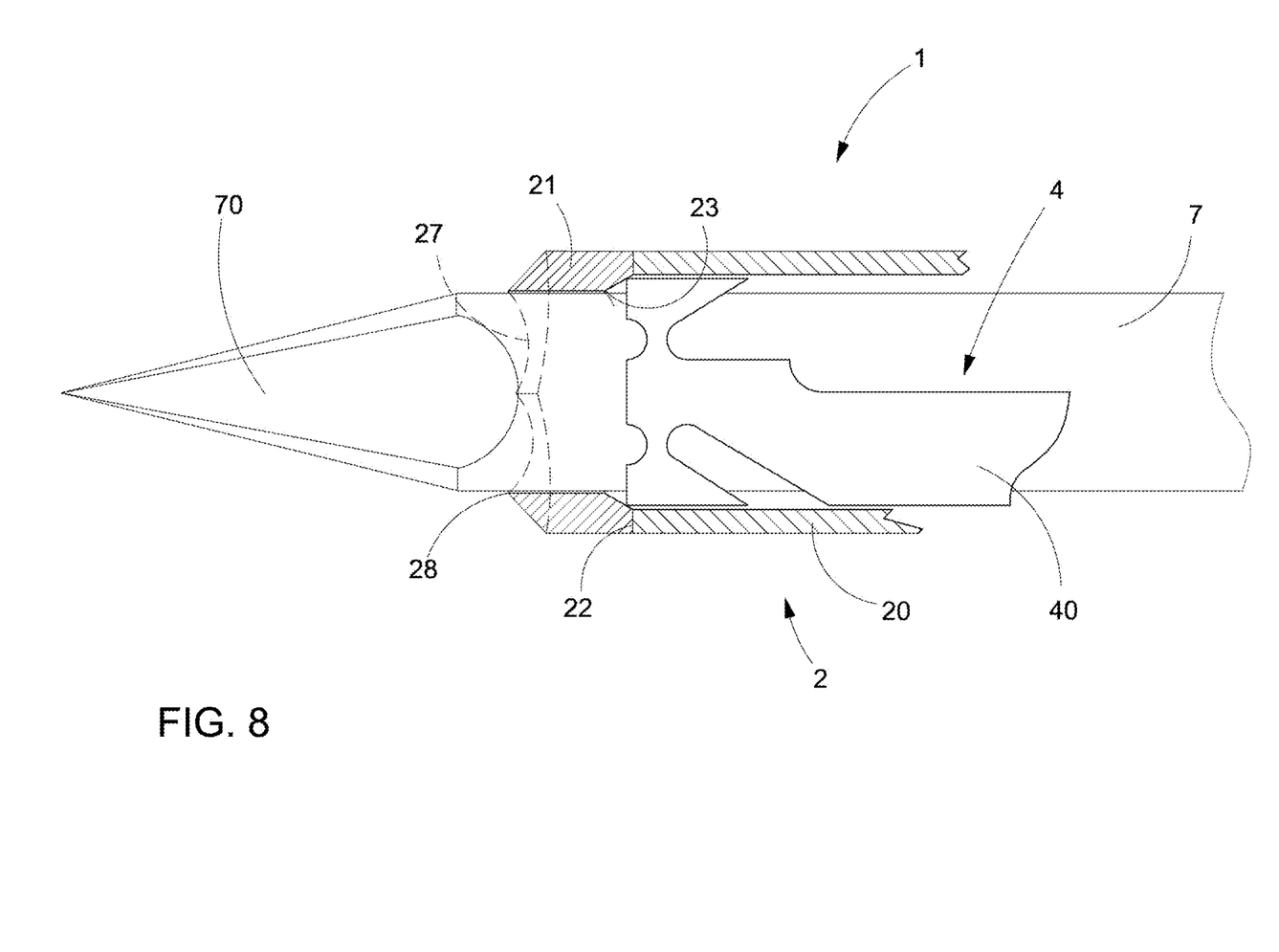
FIG. 8 is an enlarged view of the tip of the device of FIG. 1, in which the mouth of the cannula is shown in axial section.
Figure 18:
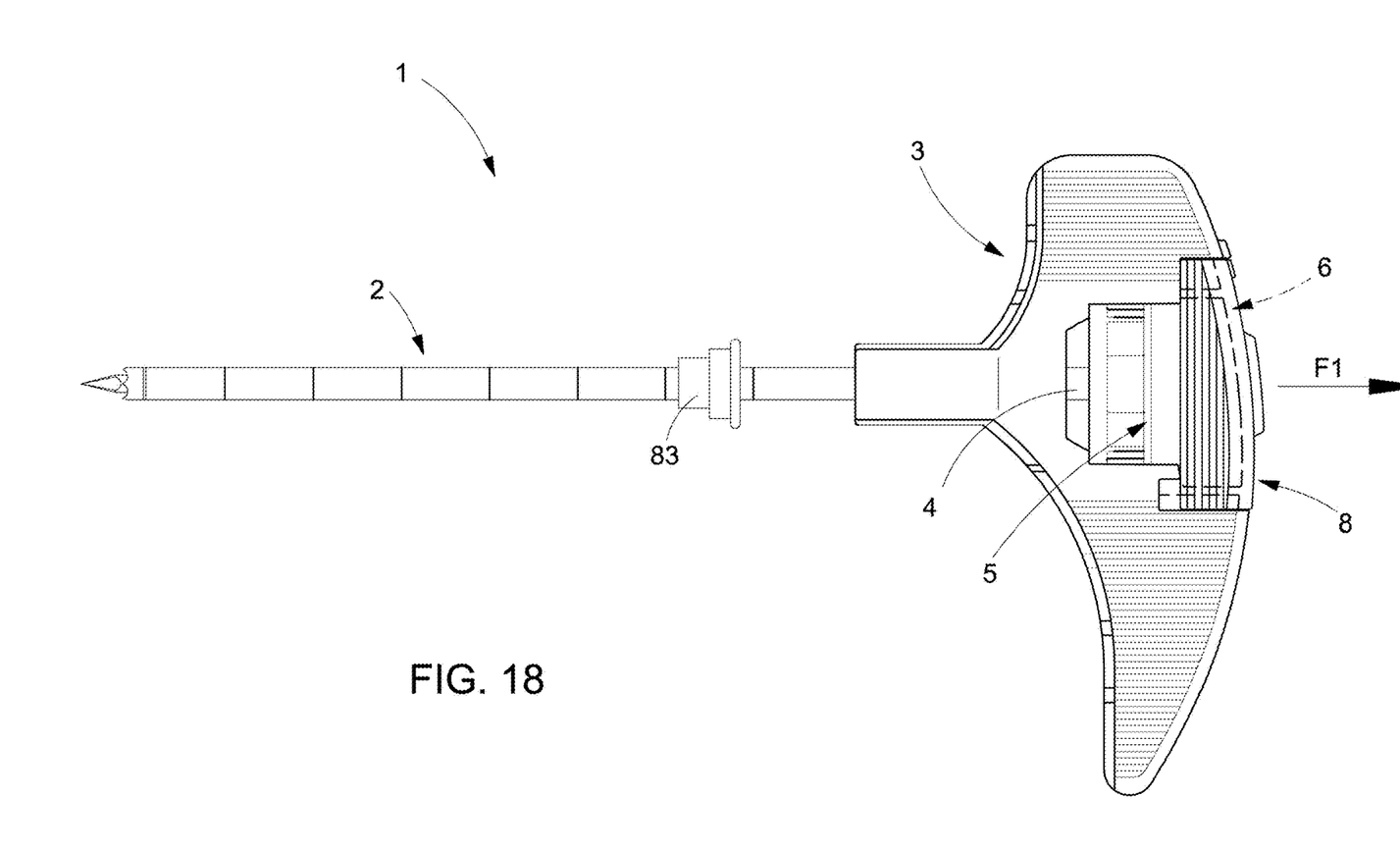
FIG. 18 is a side view of the bone biopsy device of FIG. 1 assembled, in position ready to pierce the bone.

As shown in FIGS. 8 and 18, the device 1 is initially provided in compact mode, with the plate 4 disposed inside the outer cannula 2 and the stylet 7 disposed inside the plate 4.

In this condition the tip 70 of the stylet protrudes from the mouth 21 of the cannula.

The anchorages 42, 43 disposed at the distal end of the plate 4, on the other hand, are inside the cylindrical part 20 of the cannula, near the end of joining 22 with the mouth 21 of the cannula 2 (FIG. 8). The latch 6 is in a closed position, thus the plate 4 cannot move from the position illustrated in FIG. 8.

The physician grips the handgrip 3 and carries out perforation of the compact part of the bone, by means of the tip 70 of the stylet, which acts as a guide for the cutting edge 27 of the mouth. When the mouth 21 arrives in proximity to the spongy part of the bone, the physician grips the closing support 8 and pulls it in the direction of the arrow F1, so as to extract the stylet 7. At this point the surgeon can advance the device 1 further, so that the mouth 21 of the cannula resects a cylindrical frustule of spongy bone.

Figure 19:
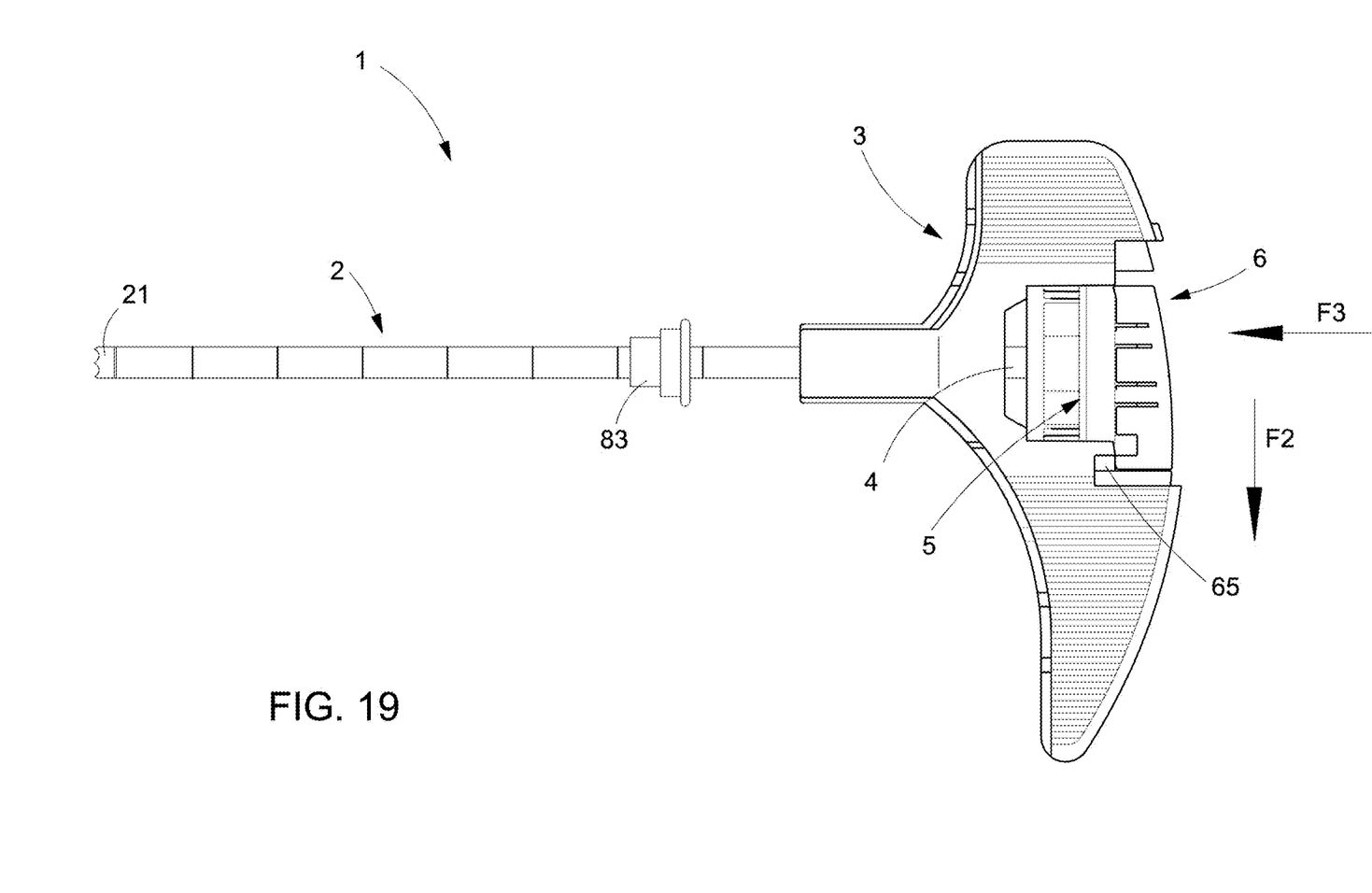
FIG. 19 is a side view of the bone biopsy device of FIG. 18, in which the stylet has been removed and the plate for collection of a sample of spongy bone has been activated.

As shown in FIG. 19, after resection of the frustule, the surgeon moves the latch 6 in the direction of the arrow F2, so as to bring the rib 65 of the latch level with the seat 37 of the handgrip, freeing the latch 6. The physician can then push the latch 6 in the axial direction of the arrow F3, at the same time also pushing the support 5 and the plate 4. The wings 52 of the support 5 bend elastically inwards and the groove 52' of the wings is snap released from the rib 36 of the guides 35 of the handgrip allowing the operator to push the support 5 integral with the plate 4 to its full extent with the latch 6. A click audible to the operator warns him that the distal end of the semi-cylindrical part 41 of the plate 4 has entered the mouth, reaching the end of its stroke and thus that the anchorages 42 and 43 of the plate have gripped the base of the frustule.

As mentioned previously, the semi-cylindrical part 41 of the plate 4 advances within the channel 25 of the cannula 2 and the two anchorages 42 and 43 placed in the distal end of the semi-cylindrical part 41 of the plate 4 bend respectively towards the interior of the cylindrical body 41 and inside the slot 44, when they encounter the tapered narrowing 23 defined by the mouth 21, acting as jaws which grip the base of the sectioned frustule, similarly to the grips of hinge pliers.

As a result the lunettes 42 and 43 come to clasp the base of the sectioned frustule firmly. The tapering of the narrowing 23 within the cannula ensures a gradual radial bending of the lunettes 42 and 43, with respect to a horizontal plane, causing the occlusion of the lumen 49 of the semi-cylindrical portion 41 so as to allow the gripping and the removal of the frustules.

At this point, the operator pulls the support 5 of the plate axially. In this manner, the plate 4 is extracted from the cannula 2 and the sectioned frustule remains anchored to the semi-cylindrical part 41 of the plate, since the base of the frustule is retained firmly by the anchorages 42 and 43 of the plate.

It should be noted that this operation leads to smaller damage to the frustule with respect to known devices, in that not clasped by tips as for example in the case of the device described in EP2215971.

Furthermore, frustule loss is practically nil, even in the most disparate cases of frustule consistency (almost liquid spongy bone or extremely hard spongy bone). It should be noted that this operation requires only axial advancement of the cannula 2, without any oscillatory luxating movement, to cause the necessary break at the base of the frustule.

Once the plate 4 has been extracted from the cannula 2, the frustule sample is removed from the cylindrical part 41 of the plate, possibly with the help of the tip 70 of the stylet 7. It should be noted that the device according to the invention does not require the use of a further instrument, such as a probe, for removal of the sampled frustule from the cannula.

Furthermore, with the device according to the invention it is possible to sample a very long frustule, with a length equal to about the length L2 of the semi-cylindrical part 41 of the plate, that is, a frustule greater than 2 cm, preferably about 3 cm. In this manner the relationship between the cortical portion and the spongy portion is more favourable for all the laboratory analyses required.

During this operation of removing the frustule, the cannula 2 is left in place, since it can be used for sampling the blood marrow (blood) from the spongy part of the bone.

Figure 20:
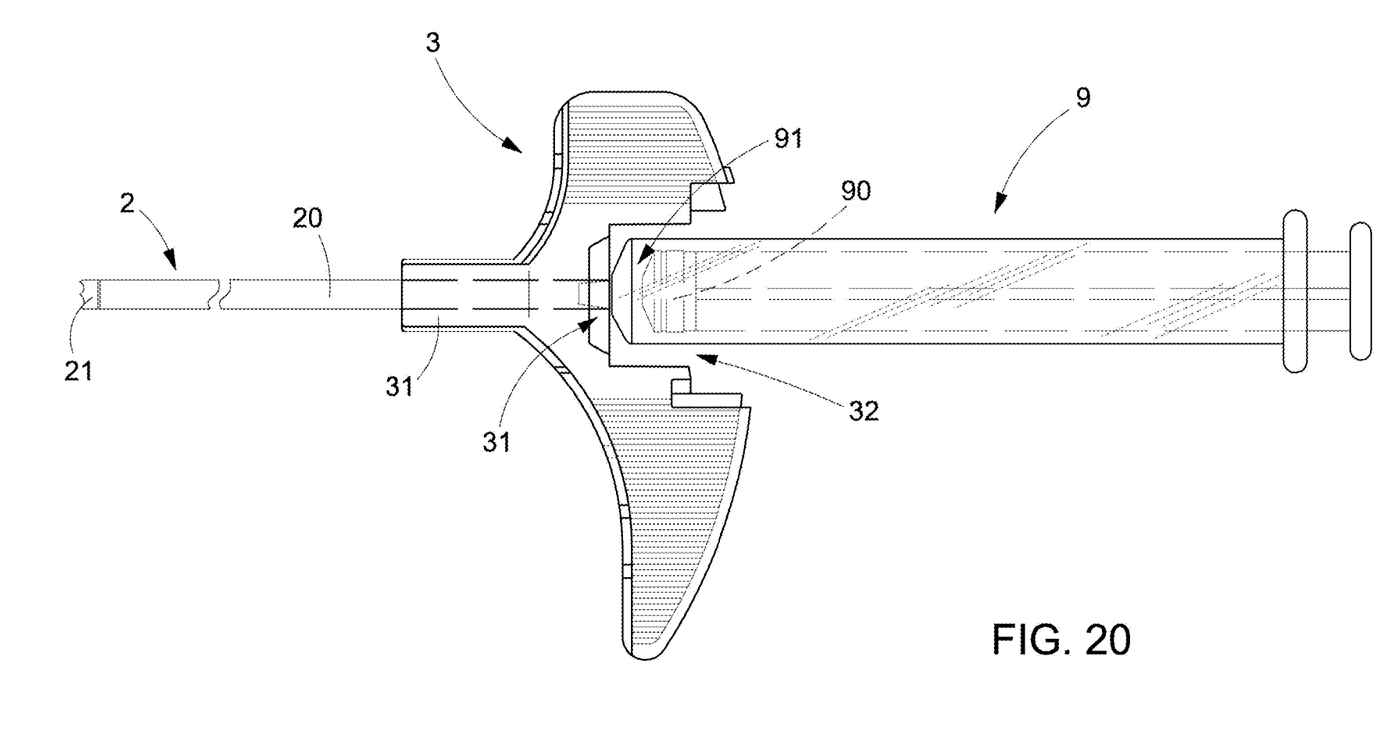
FIG. 20 is a side view of the bone biopsy device of FIG. 19, in which the plate has been removed and a syringe has been coupled for the collection of a sample of marrow from the spongiosa.

In fact, as shown in FIG. 20, the operator can insert the tip of an aspirating medical device, such as a syringe 9, for example, into the Luer Lock cone 31 of the handgrip 3, afferent to the cannula 2. Then, by operating the piston 90 of the syringe, the blood present in the spongy part of the bone is aspirated, through the cannula 2, into the chamber 91 of the cylinder of the syringe 9.

It should be noted that the device 1 according to the invention makes it possible to carry out marrow sampling, after frustule sampling, thus without depriving the frustule of blood cells which are important for the analyses to be performed.

Numerous changes and modifications of detail within the reach of a person skilled in the art can be made to the present exemplifying embodiment of the invention without thereby departing from the scope of the invention as set forth in the appended claims.

The invention claimed is:

1. A bone biopsy device (1), comprising:
an outer cannula (2) provided with a mouth (21) with a cutting edge (27) to section a frustule of spongy bone;
a plate (4) mounted slidably inside the cannula (2), a distal end of said plate (4) provided with a semi-cylindrical portion (41); and
a stylet (7) mounted slidably inside the plate (4) and provided with a pointed tip (70) which protrudes from the mouth of the cannula (2) to pierce a compact part of the bone,
an inside of the said mouth (21) of the cannula having a narrowing (23) thereon,
wherein a distal end of said semi-cylindrical portion (41) a slot (44) and a continuous circular edge (46) with a lumen (49) from which a pair of cutting anchors/bezels (42, 43) comes off, said anchors/bezels (42, 43) being arranged opposite to each other with respect to a horizontal plane,
said anchors/bezels (42, 43) being adapted to bend towards an interior of the semi-cylindrical portion (41) with respect to said horizontal plane when the anchors/bezels (42, 43) encounter said narrowing (23) of the mouth, so as to obstruct said lumen (49) and clasp the base of the sectioned frustule to allow extraction of the frustule by means of the plate (4) whilst the cannula (2) is kept at the operating site.

2. The device (1) according to claim 1, wherein a pair of upper recesses (47) and a pair of lower recesses (48) are provided on said circular edge (46) of said plate (4), said upper and lower recesses being adapted to increase flexibility of said anchors/bezels (42, 43).

3. The device (1) according to claim 1, further comprising:
   a handgrip (3) fixed to a proximal end of the cannula (2) by means of a metal cylinder joined thereto by welding;
   a support (5) fixed to a proximal end of the plate (4);
   a latch (6) mounted slidably on the support (5); and
   a closing cover (8) fixed to a distal end of the stylet,
   wherein the handgrip (3) has a seat (32) adapted to accommodate said support (5) and said latch (6), and the closing cover (8) is adapted to be mounted on said latch (6).

4. The device (1) according to claim 3, wherein said cannula (2) is joined to a metal cylinder by means of welding so as to make the cannula (2) integral with the handgrip (3).

5. The device (1) according to claim 4, wherein said latch (6) is mounted slidably on said support (5) to pass:
   from a closed position, wherein a rib (65) of the latch interferes with a wall (34') of the handgrip to prevent the handgrip from being able to be pushed accidentally and cause the plate (4) to advance prematurely within the cannula,
   to an open position, wherein said rib (65) of the latch is in register with a seat (37) of the handgrip allowing the latch to be pushed to allow the plate (4) to advance within the cannula.

6. The device (1) according to claim 3, wherein said handgrip (3) comprises:
   a cylindrical tang (30) in which a metal cylinder welded to the proximal end of the cannula (2) is fixed, and
   a frustoconical connector (31) of the Luer Lock type, disposed inside said tang (30) and accessible from said seat (32) of the handgrip to accommodate a tip of a medical aspiration instrument in order to aspirate blood marrow from the spongy bone.

7. The device (1) according to claim 3, wherein said handgrip (3) has an ergonomic shape, comprising a first, shorter handgrip portion (33) and a second, longer handgrip portion (34) between which is formed said seat (32) to accommodate said support (5) of the plate and said latch (6) and said closing cover (8) of the stylet, joining the first and second handgrip portions (33, 34) whilst maintaining a continuity of radius of curvature of a proximal surface of the handgrip.

8. The device (1) according to claim 1, wherein said cannula (2) has centimeter-markings and is equipped with a stopper that slides over the cannula and is positionable at the discretion of the surgeon to a distance from the patient's skin, said element (83) being adapted to stop ire penetration of the cannula (2) into the bone in correspondence of a desired depth during coring of frustule.

9. The device (1) according to claim 2, wherein said narrowing (23) of the mouth (21) of the cannula is tapered to allow gradual bending of the anchors/bezels (42, 43) of the plate, respectively, within said semi-cylindrical portion (41) and said slot (44) of the cannula (2).

10. The device (1) according to claim 9, wherein the edge of the mouth (21), which is fixed, by means of laser welding (22), to a tube (20) of the cannula, has a flared portion (23) which generates said tapered narrowing.

11. The device of claim 6, wherein the medical aspiration instrument is a syringe.

12. The device (1) according to claim 1, wherein said narrowing (23) of the mouth (21) of the cannula is tapered to allow gradual bending of the anchors/bezels (42, 43) of the plate, respectively, within said semi-cylindrical portion (41) and said slot (44) of the cannula (2).

13. The device (1) according to claim 12, wherein said mouth (21) of the cannula consists of a cylindrical member which is welded, by laser welding (22), to a distal edge of a tube (20) of the cannula,
   said mouth (21) having an outer diameter (0) equal to an ire outer diameter ($\varphi 1$) of the tube of the cannula and an inner diameter ($\varphi 4$) smaller than an inner diameter ($\varphi 2$) of the cannula, so as to define said narrowing (23) in the passage from the cannula tube to the mouth.

14. The device (1) according to claim 12, wherein the edge of the mouth (21), which is fixed, by means of laser welding (22), to a tube (20) of the cannula, has a flared portion (23) which generates said tapered narrowing.

15. The device (1) according to claim 9, wherein said mouth (21) of the cannula consists of a cylindrical member which is welded, by laser welding (22), to a distal edge of a tube (20) of the cannula,
   said mouth (21) having an outer diameter ($\varphi 3$) equal to an outer diameter ($\varphi 1$) of the tube of the cannula and an inner diameter ($\varphi 4$) smaller than an inner diameter ($\varphi 2$) of the cannula, so as to define said narrowing (23) in the passage from the cannula tube to the mouth.

* * * * *